United States Patent [19]

Fletcher et al.

[11] 4,037,974

[45] July 26, 1977

[54] SAMPLE CELL FOR SPECTROPHOTOMETERS

[76] Inventors: Taylor C. Fletcher, 2650-1/2 Cherry Ave., Long Beach, Calif. 90806; Bruce L. Wilkinson, 5518 Norton St., Torrance, Calif. 90503

[21] Appl. No.: 648,177

[22] Filed: Jan. 12, 1976

Related U.S. Application Data

[63] Continuation-in-part of Ser. No. 515,500, Oct. 17, 1974, abandoned.

[51] Int. Cl.² ............................................. G01N 1/10
[52] U.S. Cl. ..................................... 356/246; 250/576
[58] Field of Search ............... 356/181, 244, 246, 96, 356/97; 350/96 R, 96 A; 250/227, 574, 576

[56] References Cited

U.S. PATENT DOCUMENTS

| 3,236,602 | 2/1966 | Isreeli | 356/246 |
| 3,583,817 | 6/1971 | Rachlis et al. | 356/246 |
| 3,614,242 | 10/1971 | Hrdina | 356/181 |
| 3,740,158 | 6/1973 | Bellinger et al. | 350/96 R |

*Primary Examiner*—David C. Nelms
*Attorney, Agent, or Firm*—Keith D. Beecher

[57] ABSTRACT

A sample cell is provided for spectrophotometers which is constructed to prevent stray light from being carried to the detector through the wall of the cell. This is achieved by configuring the cell wall in a manner so that it cannot function as a light pipe for the stray light, or by providing light attenuating means in the cell wall, or by providing an appropriate masking means in the wall.

6 Claims, 6 Drawing Figures

SAMPLE CELL FOR SPECTROPHOTOMETERS

BACKGROUND OF THE INVENTION

Spectrophotometric analysis is based on the absorption or attenuation of electromagnetic radiation of a particular wavelength by the sample under test. The region of the electromagnetic spectrum most useful for spectrophotometric analysis is that between 2,000 A and 300 microns. The instruments used for conducting such analysis are referred to as spectrophotometers. A simple spectrophotemeter consists of a source of radiation; a monochromator containing a prism, grating, narrow band filter, or the like, which disperses the radiation from the source so that only a limited wavelength range is allowed to pass through the sample; a cell containing the sample; and a detector, such as a photocell, which measures the amount of light transmitted through the sample.

Any light reaching the detector which does not pass through the sample itself is considered to be "stray" light, and this stray light produces errors in the readings by the detector. Stray light can result from light which enters the side wall of the sample cell at the source end and which leave at the detector end, with the side wall acting as a light pipe. Stray light can also result when the light entering the sample cell is not completely collimated or is scattered by the sample, so that some of the light enters the side wall of the cell at the proper angle to establish a semi-light pipe condition in the side wall.

Stray light can become a significant problem in many spectrophotometric analyses. For example, in some spectrophotometric applications, high light attenuation by the sample of the order of $1:10^3 - 1:10^4$ are encountered. In such applications, even if only one part in $10^5$ of the light beam enters the side wall of the cell to be conducted thereby to the detector, errors of the order of 1-10% may result in the detector reading.

DETAILED DESCRIPTION OF THE ILLUSTRATED EMBODIMENTS

Figure 1:
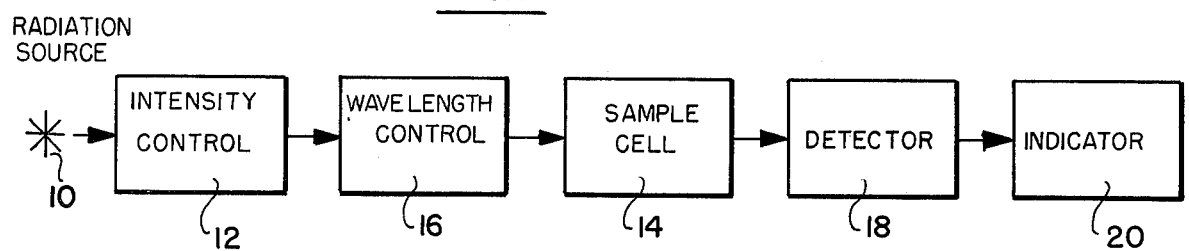
FIG. 1 is a block diagram of a typical spectrophotometer used for making spectrophotometric analyses.

The spectrophotometer shown in block form in FIG. 1 includes, for example, a source of radiation 10 which may, for example, be an incandescent lamp, a hydrogen arc lamp, or other appropriate source. THe radiation from the source is directed as a beam through an intensity control represented by the block 12. The intensity control, for example, may be an iris diaphragm, a variable slit, or it may be a rheostat in the circuit of the source 10.

The intensity control 12 directs a light beam to a sample cell 14 through a wavelength control 16. The wavelength control, for example, may be a color filter, or a prism or grating type of monochromator. The light from the wavelength control is passed through the sample in the cell 14 to a detector 18. The detector, for example, may be a photocell, a thermopile, a bolometer, or the like. The detector 18 normally produces an electric output which is applied to an indicator 20 which may take the form, for example, of a galvanometer, a pen recorder, an oscilloscope, or the like.

As mentioned above, any light which reaches the detector 18 that does not pass through the sample itself is considered stray light, and such stray light creates errors in the detector readings.

Figure 2A:
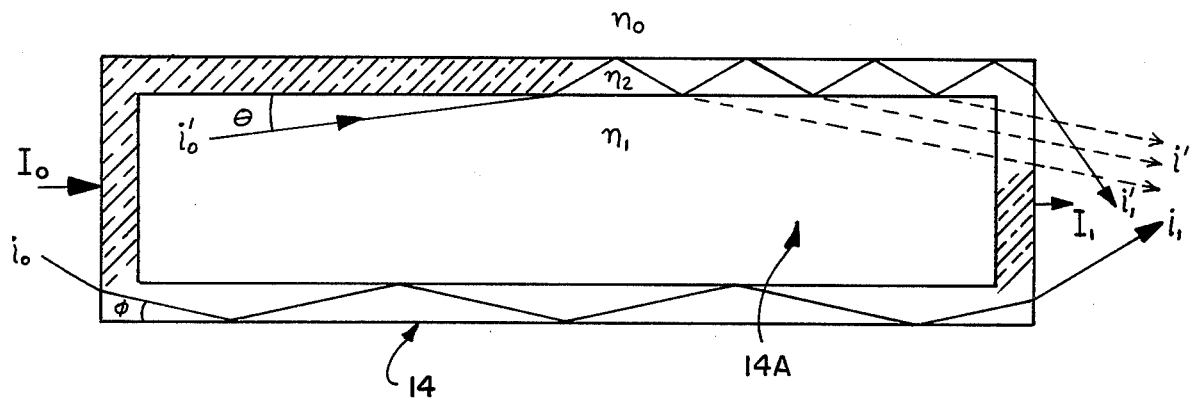
FIG. 2A is a side section of a typical prior art cell in which the sample being tested is contained.

It is usual in the prior art for the sample cell 14, in some applications, to have a configuration such as represented in FIG. 2A, and to contain a sample 14A. The sample cell 14 is constructed of a single homogenous transparent material, and it has an entrance end shown to the left of FIG. 2A and an exit end shown to the right of FIG. 2A through which a beam of radiation enters and leaves the cell and passes through the sample contained in the cell. The cell 14 also has a side wall of transparent material which is integral with the entrance end and the exit end, and which tends to form a radiation pipe which would tend to pass radiation from the beam directly to the exit end of the cell. It is the intendment of the present invention for the side wall to include means for minimizing the passage of radiation through the side wall to the exit end of the cell by llight pipe effect.

The beam of radiaton $I_0$ from the wave length control 16 enters the sample cell 14 at the left end, and emerges as beam $I_1$ at the right end to be directed to the detector 18.

Portions of the light in beam $I_0$, designated $i_o$ and $i_o'$, as shown in FIG. 2A, enter the side wall either directly from the left end of the cell ($i_0$) or enter within the side wall from the inside of the cell ($i_o'$) and exit respectively as $i_1$ and $i_1 40$. In many instances, the medium surrounding the cell and the smaple 14A are both water with an index of refraction, $n_o = n_1 = 1.33$. In other instances, the medium surrounding the cell is air or a vacuum, in which case the index of refraction $n_o = 1.00$. Also, the cell material is often of a glass or a plastic such as an acrylic, whose indices of refraction are approximately 1.50.

Therefore, as shown in FIG. 2A, any light $i_o$ traveling within the side wall of the cell 14, which intersects the side wall surfaces at an angle $\phi$ less than the critical angle (i.e. – the angle of total reflection between $n_2 - n_o$, and $n_2 - n_1$) will travel to the right-hand end of the cell and be attenuated only by the absorptivity of the cell material. In this case the wall of the cell essentially forms a light pipe. Since the sample cells are typically fabricated of a material which is highly transparent at the wave-lengths of interest, the stray light conducted by the cell walls is not appreciably attenuated. Further, even if the light in the side wall intersects the wall surface at an angle greater than the critical angle, a large fraction of the light is reflected and a significant portion of this light travels within the wall for the full length of the sample cell and then passes out the detector end of the cell.

A portion of any light, $i_o'$, striking the side wall from the sample 14A of FIG. 2A, enters the side wall. FIG. 2A illustrates the path followed by this beam if $n_2 > n_1 > n_o$, and the initial angle of incidence $\theta$ between $n_1$ and $n_2$ is sufficiently small so that the angle of incidence between $n_2$ and $n_1$ causes total reflection. However, even if the angle of incidence is greater or if $n_o$ = $n_1$ (for example if both the sample and the medium surrounding the cell are primarily water) the difference in index of refraction between $n_2 - n_o$, and $n_2 - n_1$, will cause partial reflection at the side wall surfaces and thus an appreciable portion of any light entering the side wall exits at the right end of the sample cell.

The portion of $l_1$ and $i_1'$ that reach the detector is considered stray light and creates errors in the spectrophotometers.

Figure 2B:
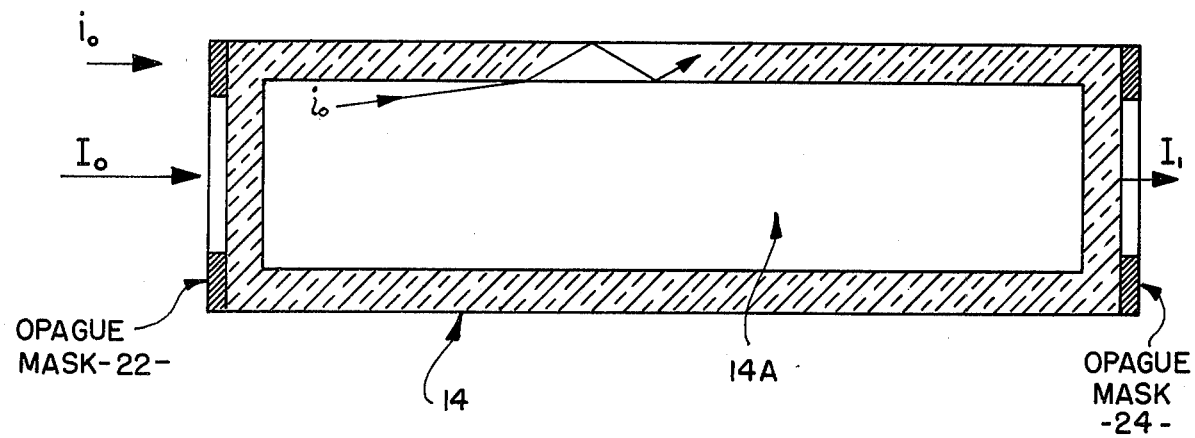
FIG. 2B shows a modification to the cell of FIG. 2A, so as to prevent stray light from being conducted by the side wall of the cell to the detector.

One approach for preventing stray light $i_1$ from reaching the detector, as shown in FIG. 2B, is to place an opaque mask 22 at the right-hand end of the cell 14A, the opaque mask having an annular configuration, so that it completely blocks the exit end of the side wall of the cell. A similar opaque mask 24 may be placed on the entrance end of the cell to prevent light from entering the wall of the cell from the entrance end of the cell.

Figure 3:
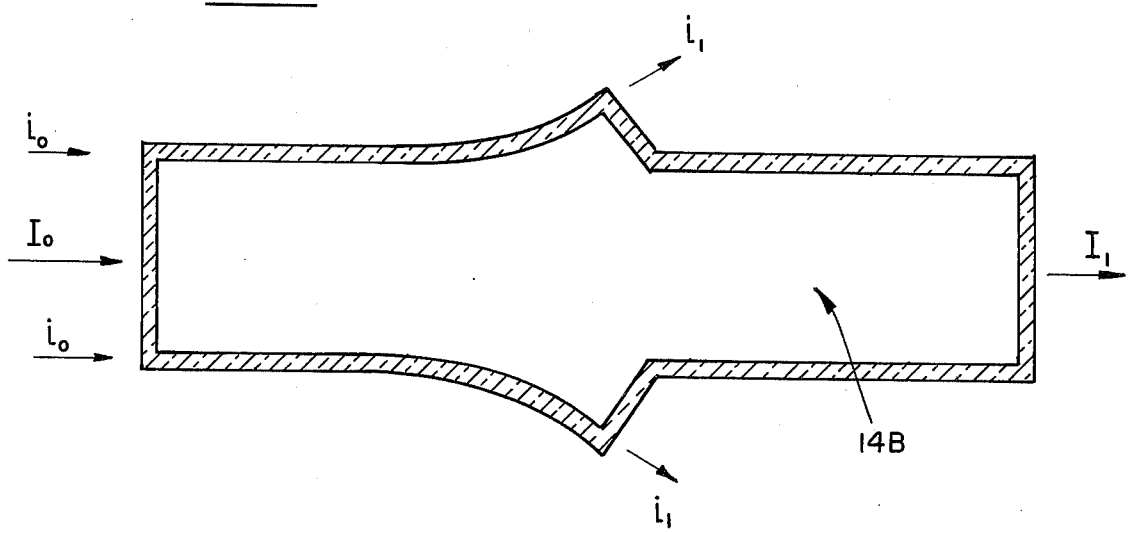
FIGS. 3, 4 and 5 show various sample cells constructed in accordance with the concepts of the invention to prevent stray light from being conducted by their side walls to the detector.

In the embodiment of FIG. 3 the sample cell 14 has a configuration designated 14B in which the side wall is turned outwardly in the illustrated manner, so that stray light is directed away from the detector, as illustrated. In the illustrated embodiment of FIG. 3, the cell wall is curved outwardly from the entrance end, as shown, and then is turned sharply inwardly (preferably at about a 90° angle) so that the stray light may be removed from the walls of the cell.

Figure 4:
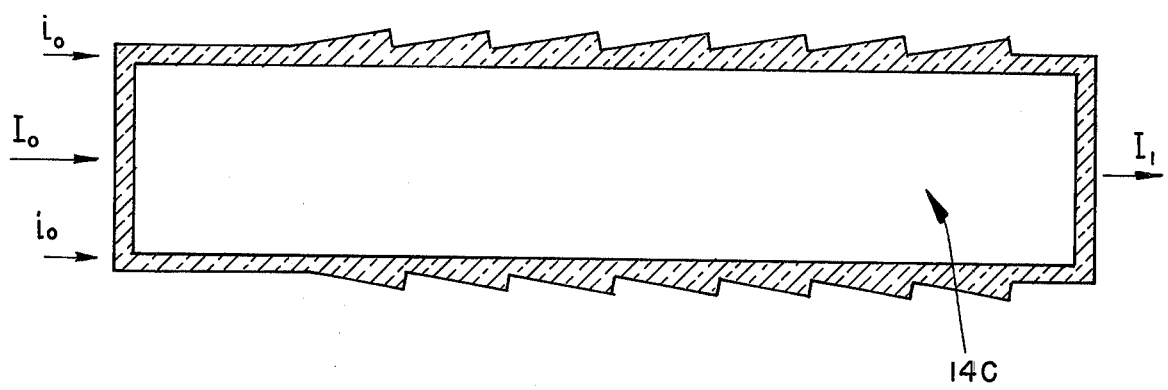

In the embodiment of FIG. 4, the sample cell 14 of FIG. 1 has a configuration designated 14C, in which the outer surface of the side wall has an essentially sawtooth configuration. In the cell of FIG. 4, the stray light entering the side wall at the entrance end of the cell will either pass outwardly from the wall of the cell, such as in the embodiment of FIG. 3, or will be reflected back to the source by the corner reflector formed by the sides of each sawtooth element. These angles are typically at 90°, as shown, however, they can be as little as 30°, and still function as an effective destroyer of light pipe characteristics in the side wall of the sample cell. Any light entering the side wall of the sample cell of FIG. 4 from the interior of the cell will, due to the sawtooth configuration of the outer surface of the cell be either reflected back into the sample, or will pass out through the wall of the cell.

Figure 5:
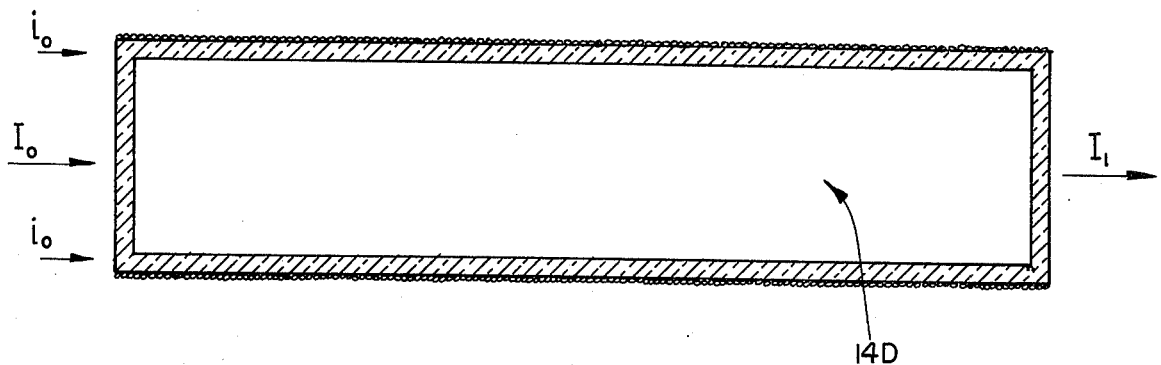

The sample cell 14 of FIG. 1 has a configuration 14D in the embodiment of FIG. 5, in which the outer surface of the side wall of the cell is frosted. The internal surface of the side wall also could be frosted, but frosting of both surfaces of the side wall is not essential. The frosting on the surface of the side wall of cell 14D can take any appropriate form, such as vertical lines or scratches.

The cell 14B of FIG. 3 has certain advantages of the other cells illustrated herein in that essentially all the stray light is removed, whereas the other cells allow a residual portion of the stray light to travel along the side walls to the exit end of the cells. The cells 14C and 14D of FIGS. 4 and 5 are somewhat more effective than the cells of FIGS. 2B and 3 in attenuating light entering the side wall of the cells from the sample itself, as shown in FIG. 2A.

As an alternative approach, the cell itself may be fabricated of a material which absorbs light at the wavelength being used, so that any light tending to pass along the length of its side wall is attenuated. However, this also produces unwanted attenuation at the entrance and exit ends of the cell.

Typically, the main light beam $I_0$ will pass through a cell window whose thickness is less than 5% of the cell length, giving a 10% total for both the entrance and exit ends of the cell. Therefore, if the light beam is attenuated 2:1 by the windows in the entrance and exit ends of the cell, the absorption in the sides of the cell will be of the order of 1,000:1, or a net improvement of 500:1 in the main beam to stray light intensity ratio.

Another alternative would be to coat one or more surfaces of the cell with an appropriate material so as to reduce the reflectivity of the surface. The material is selected to have an index of refraction which lies between the index of refraction of the cell material ($n_c$), and the index of refraction of the surrounding medium ($n_m$). Typically the coating should have an index of refracton of the order of $\sqrt{n_c n_m}$. The coating then serves to reduce the percentage of non-collimated light reaching the detector.

Although the aforesaid coating will not necessarily change the critical angle of the cell walls, it will serve to reduce the reflectivity of the walls below the critical angle allowing more of the stray light to escape and thereby to inhibit the travel of stray light down the walls to the detector.

Although masking the ends of the sample cell, such as shown in FIG. 2B is often effective for preventing stray light to reach the detector, an advantage of the cells shown in the other embodiments of the invention, which do not use masks, is that such cells may be formed of a single homogeneous, transparent material in a single operation, such as by injection molding, or in the case of the coated cell, by a simple second process.

The invention provides, therefore, a simple construction for a sample cell for use in a spectrophotometer, by which stray light is prevented from reaching the detector with sufficient magnitude to create significant errors in the detector readings.

It will be appreciated that while particular embodiments of the invention have been shown and described, modifications may be made. It is intended in the claims to cover the modifications which fall wihtin the spirit and scope of the invention.

What is claimed is:

1. A sample cell constructed of a single homogeneous material for use in spectrophotometers having an entrance end and an exit end through which a beam of radiation enters and leaves the cell and passes through a sample contained in the cell, the cell having a transparent side wall, a first window at the entrance end integral with said side wall and of the same material as said side wall, a second window at the exit end integral with said side wall and of the same material as said side wall, and said side wall including means for minimizing the passage of the radiation through said side wall from the entrance end to the exit end of the cell so as to obviate the formation of a light pipe by said side wall.

2. The sample cell defined in claim 1, in which said means includes an outwardly curved intermediate section of the side wall for reducing the internal reflectivity of the side wall below the critical angle thereof.

3. The sample cell defined in claim 1, in which said means includes a sawtooth-shape outer surface of the side wall for reducing the internal reflectivity of the side wall below the critical angle thereof.

4. The sample cell defined in claim 1, in which said means includes at least one frosted surface on the side wall.

5. The sample cell defined in claim 1, in which said means includes a coating on at least one surface of the side wall of material of an index of refraction lying between the respective indices of refraction of the side wall and of the surrounding medium.

6. The sample cell defined in claim 1, in which said means includes a radiation attenuating material forming such side wall.

* * * * *